(12) United States Patent
Huang

(10) Patent No.: US 10,418,411 B2
(45) Date of Patent: Sep. 17, 2019

(54) MULTISPECTRAL IMAGING DEVICE

(71) Applicant: EXPANTRUM OPTOELECTRONICS, Shanghai (CN)

(72) Inventor: Zhongshou Huang, Shanghai (CN)

( * ) Notice: Subject to any disclaimer, the term of this patent is extended or adjusted under 35 U.S.C. 154(b) by 0 days.

(21) Appl. No.: 15/815,852

(22) Filed: Nov. 17, 2017

(65) Prior Publication Data
US 2018/0358400 A1    Dec. 13, 2018

(30) Foreign Application Priority Data

Jun. 13, 2017    (CN) .......................... 2017 1 0441874

(51) Int. Cl.
| | |
|---|---|
| *H01L 27/146* | (2006.01) |
| *H01L 31/105* | (2006.01) |
| *H01L 31/103* | (2006.01) |
| *H01L 31/0376* | (2006.01) |
| *H01L 31/0224* | (2006.01) |
| *A61B 5/00* | (2006.01) |

(52) U.S. Cl.
CPC ...... *H01L 27/14652* (2013.01); *A61B 5/0075* (2013.01); *A61B 5/489* (2013.01); *H01L 27/1461* (2013.01); *H01L 27/1463* (2013.01); *H01L 27/14612* (2013.01); *H01L 27/14647* (2013.01); *H01L 31/022466* (2013.01); *H01L 31/03762* (2013.01); *H01L 31/103* (2013.01); *H01L 31/1055* (2013.01); *A61B 2562/0238* (2013.01); *A61B 2562/043* (2013.01)

(58) Field of Classification Search
CPC ......... H01L 27/14652; H01L 27/14645; H01L 27/14649; H01L 27/1465; H01L 27/14667; H01L 27/14669; H01L 27/1467
See application file for complete search history.

(56) References Cited

U.S. PATENT DOCUMENTS

| | | | | |
|---|---|---|---|---|
| 5,113,076 A | * | 5/1992 | Schulte ............... | H01L 27/1446 250/330 |
| 5,769,384 A | * | 6/1998 | Baumgartner .... | H01L 27/14643 250/214 A |
| 6,606,120 B1 | * | 8/2003 | Merrill .............. | H01L 27/14645 250/226 |
| 10,211,252 B2 | * | 2/2019 | Huang .............. | H01L 27/14652 |
| 10,249,662 B2 | * | 4/2019 | Huang .............. | H01L 31/03762 |
| 10,281,323 B2 | * | 5/2019 | Sato ........................ | G01J 1/429 |
| 10,281,597 B2 | * | 5/2019 | Tredwell ........... | H01L 27/14663 |
| 10,283,554 B2 | * | 5/2019 | Jin .................... | H01L 27/14647 |

(Continued)

*Primary Examiner* — Victoria K. Hall

(57) ABSTRACT

A multispectral imaging device comprises a hybrid semiconductor device of stacked type to separate different light wavebands in a three-dimensional space, said hybrid semiconductor device comprises: a first photodiode, to convert NIR light photons to electrons, said first photodiode forming a detecting array of infrared light image, said first photodiodes comprising a substrate and an depletion layer; and a second photodiode, arranged on said first photodiode, to convert visible light photons to electrons, said second photodiode forming a detecting array of visible light image. The multispectral imaging device provided by the present disclosure decreases the cross-talk between different photodiodes and increases the total performance.

14 Claims, 12 Drawing Sheets

(56) References Cited

U.S. PATENT DOCUMENTS

| | | | |
|---|---|---|---|
| 2004/0108564 A1* | 6/2004 | Mitra | H01L 27/14649 257/442 |
| 2009/0200589 A1* | 8/2009 | Qian | H01L 27/14603 257/292 |
| 2010/0090093 A1* | 4/2010 | Shim | H01L 27/14632 250/208.1 |
| 2011/0108728 A1* | 5/2011 | Chang | G01J 1/02 250/338.4 |
| 2013/0077958 A1* | 3/2013 | Xu | G03B 11/00 396/544 |
| 2013/0235178 A1* | 9/2013 | Wang | H04N 5/33 348/77 |
| 2013/0322729 A1* | 12/2013 | Mestha | A61B 5/02 382/134 |
| 2017/0162602 A1* | 6/2017 | Saitoh | H01L 29/78648 |
| 2017/0302870 A1* | 10/2017 | Ikuma | H04N 5/357 |
| 2017/0309684 A1* | 10/2017 | Yamada | H01L 51/44 |
| 2017/0353673 A1* | 12/2017 | Roy | H01L 27/14614 |
| 2017/0363722 A1* | 12/2017 | Yonehara | G01S 7/4816 |
| 2018/0069046 A1* | 3/2018 | Jin | H01L 27/14621 |

\* cited by examiner

MULTISPECTRAL IMAGING DEVICE

CROSS REFERENCE

This application is based upon and claims the benefit of priority from Chinese Patent Application No. 201710441874.4, filed on Jun. 13, 2017, the entire contents thereof are incorporated herein by reference.

TECHNICAL FIELD

The present disclosure belongs to the field of medical diagnosis instrument, specifically to a multispectral imaging device.

BACKGROUND

Subcutaneous structure and blood vessels under skin are barely visible for naked eyes directly. Without any medical instrument, medical doctors can only rely on the external outline of human body and their anatomic knowledge to recognize and locate subcutaneous structures and blood vessels.

The blood vessels, comprising veins and arteries, are hidden below the epidermis and dermis, and in some cases mixed with the subcutaneous fat or are even behind the bones. Images of the blood vessels under the visible light illumination are therefore extremely faint and barely visible for naked eyes. Before puncture, the doctors often try to make the blood vessels more visible by asking the patients to clench their fist or flapping the skin above the blood vessel, but hindered by patients' age and the thickness of subcutaneous fat and etc., the visibility of subcutaneous blood vessels is still not satisfying in most cases. Injections relying on the barely visible images of blood vessels frequently results misalignment of the puncture, causing unnecessary pain in patients and delaying optimal time for medical treatment, even triggering other serious side effects. Apart from blood drawing and injection acted on blood vessels directly, acupuncture and other medical surgery etc. all need the blood vessels to be located accurately, so the blood vessels can be avoided or be treated respectively.

In recent years, a technical approach for solving the problem based on near-infrared (NIR) imaging technology has been proposed. This technical approach is based on the fact that the absorption coefficient of hemoglobin for near infrared from 760 nm and 1000 nm is different from other human tissues around the veins, so image contrast is built up. To implement this technical approach, NIR images of veins are acquired in the first step, then the infrared image is digitized and enhanced in contrast and signal to noise ratio by an image processing unit, enhanced image is finally projected back to human skin surface by a visible light projection device. In this technical approach, which has an augmented reality effect in a broad meaning, the doctors and nurses are able to recognize and locate precisely the subcutaneous blood vessels and conduct various medical treatments and operate in real time.

However, the subcutaneous blood vessels are surrounded by subcutaneous fat and muscular tissues, inevitably causing strong scattering to the infrared image. To add more obstacles, wrinkles, scars and hairs on the skin surface all have strong absorption and scattering effects to attenuate and blur the infrared image. These drawbacks become severe when imaging objects are narrow branches of blood vessels and capillaries. This is simply because that less blood volume and therefore less hemoglobin are in the infrared light path, while the light scatterings from surrounding tissues remain the same, resulting in less absorption and faint contrast in the infrared image. Under the influence of scattering light, the image contrast of the blood vessels to the surrounding tissues is often observed in the range of 0.01 to 0.1.

Due to the optical property of subcutaneous soft tissues, the absorption depths of a subcutaneous layer to different light wavebands are different, in the way of a penetrated depth increasing with the wavelength. The visible light waveband from 420 nm in a color of violet to 550 nm most sensitive to eyes can only penetrate 0.6 mm of epidermis layer, while the red light waveband larger than 690 nm can penetrate epidermis and corium layers to irradiate subcutaneous tissues and partial veins. NIR light waveband from 760 nm to 1000 nm, barely visible for naked eyes, can irradiate deeper subcutaneous tissues and fat layer.

When irradiating the skin, scattered light and reflected light from skin surface will cause cross-talk or noise to images of subcutaneous blood vessels. An image only showing deeper subcutaneous layers can be extracted by removing visible light image information from an original image, which is the principle of digital subtraction technology of infrared light image.

SUMMARY

The primary purpose of the present disclosure is to provide a multispectral imaging device, to reduce cross-talk between different photodiodes and to enhance overall performance of the imaging device.

According to one aspect of the present disclosure, a multispectral imaging device comprising a hybrid semiconductor device of stacked type to separate multiple wavebands in a three-dimensional space is provided, the hybrid semiconductor device comprises: a first photodiode, to convert NIR light photons to electrons, the first photodiode forming a detecting array of infrared light image, the first photodiode comprising a substrate and an electron and/or hole depletion layer formed in the substrate; and a second photodiode, arranged on the first photodiode, to convert visible light photons to electrons, the second photodiode forming a detecting array of visible light image.

Therefore, with the arrangement of the multispectral imaging device of the present disclosure, the photoelectric conversion area of the first photodiode is completely or partially depleted during operation, to have a smaller stray capacitance between the first photodiode and the second photodiode, to reduce cross-talk between different photodiodes, and then increase the efficiency of converting signal charges to signal voltage.

BRIEF DESCRIPTION OF THE DRAWINGS

By reading the detailed description of nonrestrictive embodiment referring to the figures below, the other features, objects and advantages will be more apparent.

DETAILED DESCRIPTION

In the following, embodiments of the present disclosure will be described in detail referring to figures. The concept and its realizations of the present disclosure may be implemented in a plurality of forms, and should not be understood to be limited to the embodiments described hereafter. In contrary, these embodiments are provided to make the present disclosure more comprehensive and understandable, and so the conception of the embodiments may be conveyed to the person skilled in the art fully. Same reference numbers in the figures refer to same or similar structures, so repeated description of them will be omitted.

The features, structures or characteristics described may be combined in any appropriate way in one or more embodiments. In the description below, many specific details are provided to explain the embodiments of the present disclosure fully. However, the person skilled in the art should realize that, without one or more of the specific details, or adopting other methods, components, materials etc., the technical approach of the present disclosure may still be realized. In certain conditions, structures, materials or operations well known are not shown or described in detail so as not to obfuscate the present disclosure.

To overcome the drawbacks of existing technology, the present disclosure provides a multispectral imaging device comprising a hybrid semiconductor device of stacked type to separate light of different wavebands in a three-dimensional space, the hybrid semiconductor device comprises: a first photodiode comprising a substrate and a depletion layer formed in the substrate, to convert NIR light photons to electrons; and a second photodiode, arranged on the first photodiode, to convert visible light photons to electrons visible light. Wherein, the vertical projection on the plane of the substrate of the depletion layer is overlapped with that of the second photodiode. When the second photodiode functions, the depletion layer is depleted.

Below embodiments of the present disclosure are described referring to a plurality of figures.

It should be stated that a plurality of embodiments described below along with their combinations and varieties, beyond doubt are within the scope of present disclosure.

Figure 1:
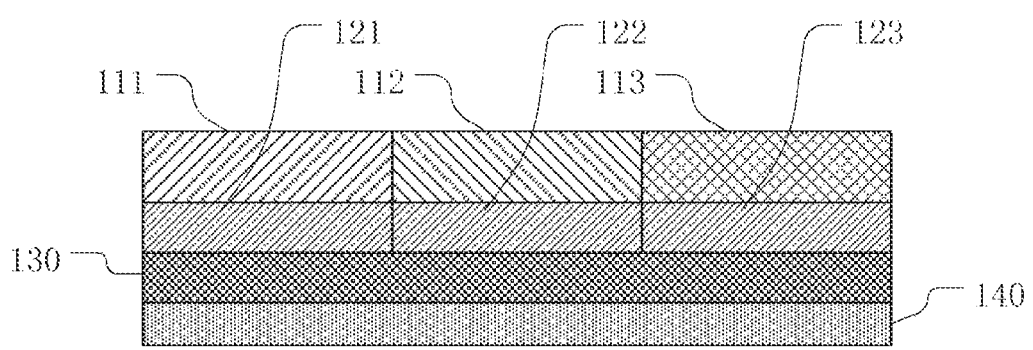
FIG. 1 is a cross-sectional view of a multispectral imaging device according to a first embodiment of the present disclosure.

FIG. 1 is a cross-sectional view of a hybrid semiconductor device according to a first embodiment of the present disclosure.

The multispectral imaging device comprises a first semiconductor layer 140 comprising a first photodiode, a second semiconductor layer comprising second photodiodes and a filtering layer.

The first photodiode is sensitive to NIR light, to convert the NIR light photons to electrons. Alternatively, the NIR light here has a wavelength ranging from 760 nm to 1000 nm.

Three second photodiodes 121, 122 and 123 arranged on the first photodiode are sensitive to visible light to convert visible light photons to electrons, and transparent for NIR light. Alternatively; the visible light here has a wavelength from 400 nm to 760 nm. The second photodiodes can be a-SiH photodiodes, the response curve of an a-SiH photodiode in visible light waveband matches nicely with the response curve of human vision system, so the visible light images acquired by the photodiodes need little color correction. As the hydrogen content, forming process and subsequent process temperature thereof vary, the a-SiH film having an energy band gap approximately from 1.6 eV to 2.0 eV has a large absorption coefficient in visible light and a much lower absorption coefficient in infrared light. As a matter of fact, an a-SiH film in 2 micrometers thick can absorb more than 95% of incident visible light. In other words, a-SiH photodiodes can convert most of visible light to electrons, and allow most NIR light to pass through to irradiate the first semiconductor layer 140.

The filtering layer is arranged on one side of the second semiconductor layer away from the first semiconductor layer 140. The filtering layer comprises a plurality of filters arranged as an array (e.g. a blue filter 111 and a red filter 112). Each filter forms a filtering section transparent for visible light in a specific color band and NIR light. In the embodiment, a plurality of filters comprise band-pass color filters transparent for visible light with shorter wavelength (e.g. a blue filter 111 transparent for light from 400 nm to 460 nm) and band-pass color filters transparent for visible light with longer wavelength (e.g. a red filter 112 transparent for light from 650 nm to 760 nm). The filtering layer can further comprise a transparent film 113 (e.g. a transparent organic film). The transparent film 113 also forms a plurality of filtering sections transparent for visible light and NIR light. The blue filter 111, red filter 112 and transparent film 113 are arranged periodically and repeatedly in two directions (e.g. two orthogonal directions) on the plane of the substrate, and form an array of filtering sections. Each filtering section corresponds to each of the second photodiodes 121, 122 and 123. Hence, when light irradiates the multispectral imaging device, blue light and NIR light pass through the blue filter 111, red light and NIR light pass through the red filter 112, visible light and NIR light pass through the transparent film and irradiate corresponding second photodiodes. Visible light photons are converted to electrons or holes in the corresponding second photodiodes and stored temperately temporarily in corresponding storage capacities till the signal charge of corresponding pixel is read out or a reset of pixel potential occurs. Meanwhile NIR light photons pass through the second semiconductor layer and are converted in the first semiconductor layer 140, and then stored temporarily in corresponding storage capacities until the signal charge of corresponding pixel is read out or a reset of pixel potential occurs.

In the embodiment, the multispectral imaging device further comprises an insulating layer 130 at least transparent for NIR light, arranged between the first semiconductor layer 140 and the second semiconductor layer, to insulate the two layers from each other.

For the sake of simplicity, FIG. 1 only shows a simplified structure of the multispectral imaging device. Those skilled in the art can add or modify certain layers or parts according to practical application and process, for example, modifying or adding the electrodes of conversion devices of the second semiconductor layer and corresponding pixel switches; modifying or adding photodiodes in the first semiconductor layer 140 and other related structure of ion implantation and diffusion layer; modifying or adding other electrodes; modifying or adding pixel switches; and modifying or adding data lines and scan lines of signal output and etc.

Figure 2:
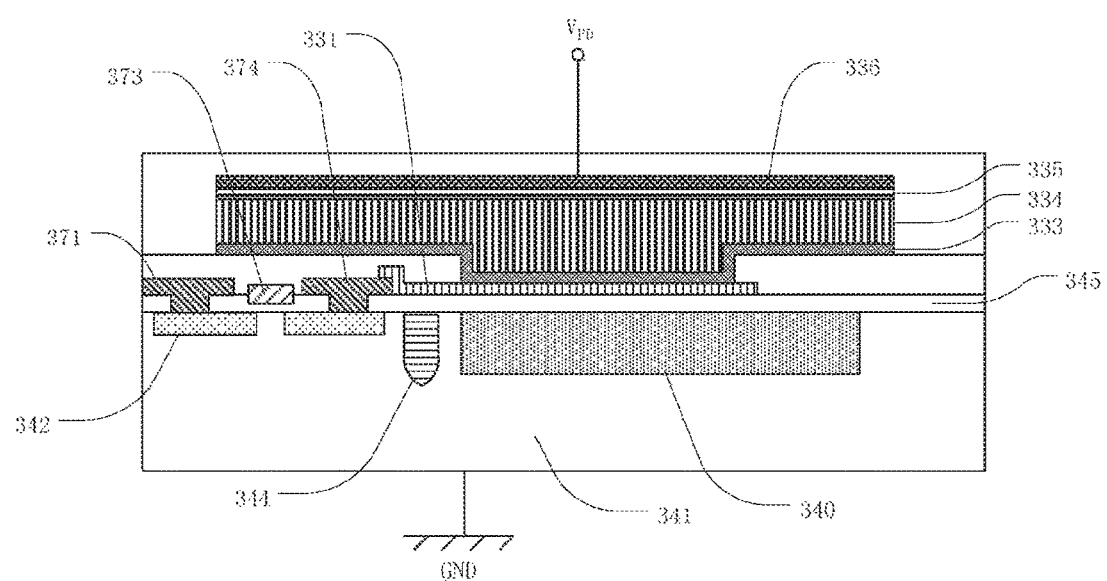
FIG. 2 is a cross-sectional view of a hybrid semiconductor device according to a second embodiment of the present disclosure.

FIG. 2 is a cross-sectional view of a multispectral imaging device according to a second embodiment of the present disclosure. The hybrid semiconductor device of stacked type in FIG. 2 comprises a first photodiode, a second photodiode arranged on the first photodiode and an insulating layer 345 of field oxide arranged between the first photodiode and the second photodiode. The equivalent capacitance of the insulating layer 345 can be indicated as $C_{OX}$.

The first photodiode comprises a substrate 341 of N type or P type and a depletion layer 340 formed in the substrate. The depletion layer 340 is correspondingly a hole depletion layer or an electron depletion layer. The equivalent capacitance of the depletion layer 340 can be indicated as $C_{DEP}$.

The second photodiode comprises a first transparent conductive film 331, a first doped layer 333, an un-doped layer 334 of amorphous silicon, a second doped layer 335 and a second transparent conductive film 336 formed on the insulating layer 345 in sequence.

The first transparent conductive film 331 is an electrode on the bottom of the second photodiodes, and the material of the electrode can be ITO, $SnO_2$ etc. The first doped layer 333 and the second doped layer 335 can be two heavy doped layers respectively arranged on the bottom and on the top of the second photodiodes. If the first doped layer 333 presents N+ type conductivity, then the second doped layer 335 should present P+ type conductivity; and vice versa. When the first doped layer 333 or the second doped layer 335 is doped with an N+ type dopant, in certain embodiments, plasma-enhanced chemical vapor deposition can be adopted by adding a certain percentage of phosphine ($PH_3$) to filming gas mainly comprising silicone ($SiH_4$). When the first doped layer 333 or the second doped layer 335 is doped with an P+ type dopant, in certain embodiments, plasma-enhanced chemical vapor deposition can similarly be adopted and a certain percentage of diborane ($B_2H_6$) gas is added to the filming gas. Considering the fact that the un-doped film 334 presents weak N type conductivity, it is preferred to add a low percentage of diborane ($B_2H_6$) gas to the filming gas to have lower dark current of the second photodiode. The second transparent conductive film 336 is an electrode on the top of the second photodiodes, and the material of the electrode can be ITO, or $SnO_2$, or other conductive material highly transparent for visible light and infrared light. The equivalent capacitance between the first transparent conductive film 331 and the second transparent conductive film 336 can be indicated as $C_{DP}$.

In the embodiment shown in FIG. 2, the multispectral imaging device further comprises a second field effect transistor, arranged between the first photodiode and the second photodiode, and functioning as a switch transistor of the second photodiode. The source electrode 374 of the second field effect transistor is connected to the first transparent conductive film 331 of the second photodiode. Shown in FIG. 2, the semiconductor layer 342 of the second field effect transistor is arranged in the substrate 341 of the first photodiode, the source electrode 374 and drain electrode 371 of the second field effect transistor are arranged between the insulating layer 345 and the second photodiode, and are connected electrically to the semiconductor layer 342. The gate electrode 373 of the second field effect transistor is surrounded by the source electrode 374, the drain electrode 371 of the second field effect transistor and the semiconductor layer 342. The source electrode 374 and drain electrode 371 of the second field effect transistor are made from a same kind of metal, e.g. Cr, Mo, Al, Cu or an alloy thereof. The material of the gate electrode 373 can be polycrystalline silicon or metal, e.g. one of the metals above or an alloy thereof. It should be stated that, FIG. 2 is only a kind of structure of the second field effect transistor, and those skilled in the art can further realize more combinations and arrangements of structure, which are beyond doubt within the scope of the present disclosure.

The multispectral imaging device further comprises an isolating component 344, arranged between the semiconductor layer 342 and the depletion layer 340 on the plane of the substrate 341. The isolating component 344 can be a shallow trench isolation (STI) component, to isolate the semiconductor layer 342 from the surrounding thereof. The advantages of the arrangement are low dark current of the substrate 341 and less signal crosstalk.

Shown in FIG. 2, the hybrid semiconductor device can have different combinations according to different variants, such as the structure of the second photodiodes from top to bottom varying between PIN and NIP type, the channel type of the field effect transistor in the first photodiode varying between N type and P type, and the type and structure of the depletion layer 340 varying. Therefore, the reset potential of the first transparent conductive film 331 also has different optimal ranges, which will be stated in detail in the following.

The depletion layer of the first photodiode can be a depletion layer with a single layer or double layers. Related to the depletion layer of a single layer, the reset potential of the conductive film 331 needs to satisfy the condition that the semiconductor below the field oxide layer is always depleted and the thickness of the semiconductor is large enough, e.g., larger than 2 micrometers. One role of the thickness required is to have higher infrared conversion efficiency; another role is to have a less capacitance $C_{DEP}$.

Related to the depletion layer of double layers, under the synergetic function of the transistor of the first photodiode and external voltage, all charges in a potential well are extracted, to completely deplete the potential well for storing photo-generated electrons or holes. The depth of the potential well depleted completely is decided by doped concentration and doped thickness. However the potential of the conductive film 331 will decrease or increase the position of the bottom of the potential well through a field oxidized layer, to influence the maximum number of charges stored in the first photodiode. Hence the reset potential of the conductive film 331 should satisfy the condition that two sides of the field oxidized layer have potentials close to each other, to have a lowest cross-talk to the first photodiode. As an example, the potential difference between the reset potential and the surface potential below the field oxidized layer is lower than IV.

Apart from the above conditions, the reset potential of the first transparent conductive film of the second photodiode should further satisfy the following three working conditions:

Firstly, the potential difference between the reset potential and the potential of the second transparent conductive film, i.e. the voltage between two ends of the second photodiode should define a wide enough dynamic range of visible light signal, the voltage according to different requirements ranges from 3V to 10V.

Secondly, the reset potential is also the initial voltage of gate electrode of a transistor with functions of amplification or conversion from charges to voltage, i.e. the bias working voltage of an amplifier transistor, must guarantee that the transistor can stay in a linearity range in the tire dynamic range of signal.

Thirdly, the cooperation of the reset potential with the gate voltage and drain voltage of a reset transistor, should guarantee that only a little leakage of signal charges stored occurs during storage period, and the little leakage can be cleaned up by the reset transistor during reset period.

When infrared light irradiates the depletion layer 340, the signal charges generated are accumulated in the potential well of the depletion layer 340, to partially fill or deplete the potential well. Further, when the potential well is completely filled, the depletion layer will no longer exist. In other words, when the second photodiode is working (during the periods of photoelectric conversion, storage, read out or reset), the electrons or the holes of the depletion layer 340 are completely or partially depleted, and the depletion layer has a thickness larger than 2 micrometers, then the equivalent capacitance $C_{DEP}$ of the depletion layer 340 is smaller.

Thicker depletion layer 340 can absorb more infrared light, and the infrared light component of longer wavelength absorbed increases. For example, in a detecting array of infrared light image formed by a plurality of first photodiodes two or three kinds of depletion layers are arranged. One role of the arrangement is to acquire infrared light of different wavebands respectively, i.e. to acquire infrared images of different "colors". Another role is to increase the dynamic range of detection aiming at stronger infrared light. In other words, when the photodiodes with thicker depletion layers are already saturated, the photodiodes with thinner depletion layers can still work in a linear response region.

Further, the present disclosure has the following advantages by decreasing equivalent capacitance $C_{DEP}$ to decrease the total capacitance of the first photodiode and the second photodiode:

1) on one hand, when the electric signal of the second photodiode is read out through the second field effect transistor, the total capacitance $C_{total}$ of the first photodiode and the second photodiode can be calculated from the following equation:

$$C_{total} = C_{PD} + \frac{C_{OX} \cdot C_{DEP}}{C_{OX} + C_{DEP}}$$

The time constant t of reading the signal out is calculated from the equation $t = C_{total} \cdot R_{on}$. Therefore, as much as possible of signal charges ($R_{on}$) can be read out within a limited time by decreasing the capacitance $C_{DEP}$ to decrease the total capacitance $C_{total}$;

2) on the other hand, the Switch Noise read out together with the signal can be calculated from the following equation: (here k refers to boltzmann constant, T refers to absolute temperature):

$$\text{Switch Noise} = \sqrt{k \cdot T \cdot C_{total}}$$

It can be seen that, the switch noise can also be decreased by decreasing the capacitance $C_{DEP}$ to decrease the total capacitance $C_{total}$.

3) thirdly, the signal voltage is inversely proportional to the total capacitance of the first photodiode and the second photodiode in a case that: each pixel comprises an active signal amplifying circuit, the photo-generated charges are converted to signal voltage to be applied to the gate electrode of an output transistor and to be output according to a scan sequence, that is, in a case adopting amplified pixel or active pixel sensor. Therefore, a higher signal voltage can be generated by decreasing the capacitance $C_{DEP}$.

In addition, influenced by the structure of the depletion layer of a single layer and the principle of MOS devices, under a certain heat balance, the minimum value of $C_{DEP}$ can be calculated by the following equation (here q refers to quantity of electron charges, $\varepsilon_0$ and $\varepsilon_s$ refer to vacuum permittivity and relative dielectric constant of silicon semiconductor respectively, $N_A$ refers to doping density of silicon substrate, $V_B$ refers to flat-band voltage):

$$C_{DEP} = \sqrt{\frac{q \cdot \varepsilon_0 \cdot \varepsilon_s \cdot N_A}{4 \cdot V_B}}$$

It can be seen from the equation that decreasing the doping density of the substrate is the most direct way to decrease the capacitance $C_{DEP}$. In a dynamic actuating mode under non-thermal equilibrium, a higher impulse voltage for reset can be applied instantaneously through the second field effect transistor to the first transparent conductive film 331, then the substrate 341 can be depleted deeper to have a lower capacitance $C_{DEP}$. However the voltage difference between the potential of the first transparent conductive film 331 and the potential $V_{PD}$ of the second transparent conductive film 36 should be large enough to satisfy the following two conditions: firstly, the second photodiode is kept always under a reverse bias state; secondly, when the intensity of the incident light gets to the highest set level, at least 0.5V voltage difference should be still left between the two ends of the second photodiode in 2 micrometers thick, to have the photo-generated charges actuated by a high enough electric field and collected on the first transparent conductive film 331 effectively.

Figure 3:
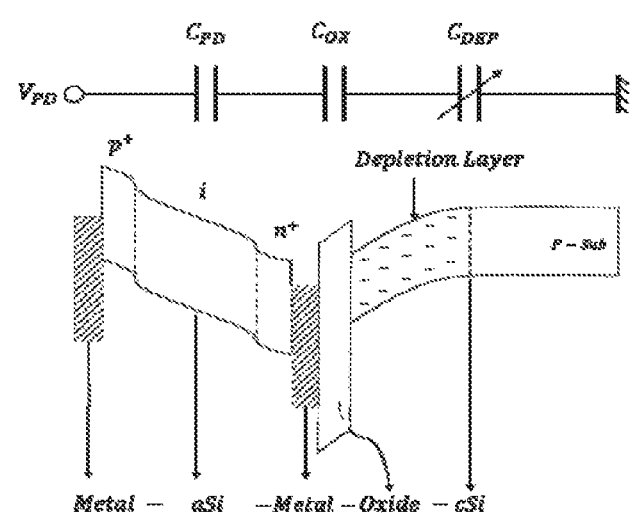
FIG. 3 to FIG. 5 show potential profiles and capacitor equivalent circuits of a hybrid semiconductor device according to different embodiments of the present disclosure, respectively.
Figure 4:
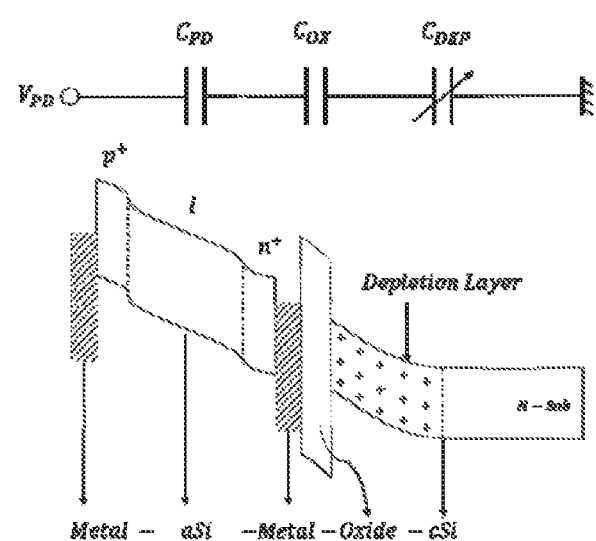
Figure 5:
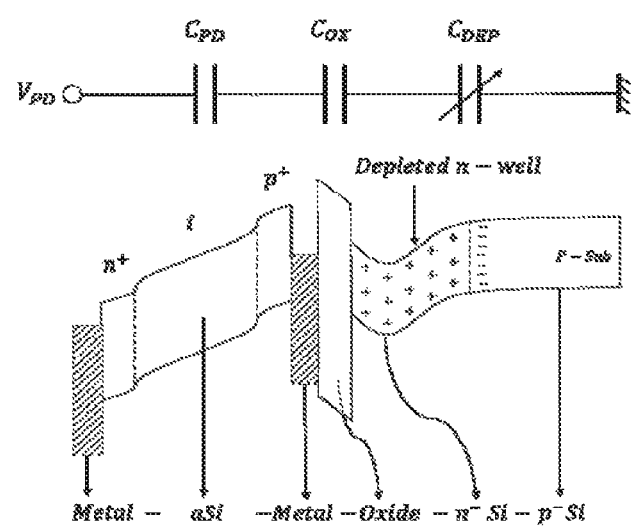

FIG. 3 to FIG. 5 are combined in the following to describe potential profiles and capacitor equivalent circuits of a hybrid semiconductor device according to different embodiments of the present disclosure.

FIG. 3 shows a longitudinal potential profile and a capacitor equivalent circuit, wherein, the second photodiode of PIN type is stacked on the first photodiode with a P type substrate. One role of keeping the middle metal electrode (i.e. a first transparent conductive film) under a high enough potential is to keep the second photodiode always under a reverse bias stage, and another role is to have a hole depletion layer with a certain thickness formed on the P type substrate. However when the intensity of the incident light is so large that the potential of the middle metal electrode is substantially pulled to $V_{PD}$, the hole depletion layer will be thinner, and even enters into a charge accumulation state, i.e. the capacitance $C_{DEP}$ is close to infinitely large. In other words, with the structure in FIG. 3, the dynamic range of the second photodiode is restricted to the profile of the surface potential of a P type substrate.

In the structure in FIG. 4, the P type substrate is replaced with a N type substrate. Once the potential of the middle metal electrode is set to any potential between $V_{PD}$ and GND, the larger the intensity of incident visible light is, the lower the potential of the middle metal electrode will be, then the thickness of the electron depletion layer in the N type substrate will be larger and cannot be decreased, to keep the capacitance coupling of the second photodiode and the N type substrate always small. Even if a field effect transistor or a crystal silicon photodiode exists in the N type substrate, the working state of the field effect transistor or the crystal silicon photodiode won't be reversed.

FIG. 5 is another kind of potential profile. By doping the P type substrate of the first photodiode lightly of N type, a N type potential well completely electron depleted is generated. One role of the structure is to generate a thicker electron depletion layer capable of decreasing capacitance; another role is to have a long enough distance to absorb infrared light, and then increase the detecting sensitivity of infrared image.

Combining FIG. 3 to FIG. 5, different combinations of different photodiodes according to a third embodiment of the present disclosure are described herein referring to FIG. 6 to FIG. 9.

In the case requiring a smaller stray capacitance between the first photodiode 240 and the second photodiode 220 and a larger dynamic range, each of the two following combinations is preferably adopted: a NIP type photodiode of amorphous silicon (second photodiode 220) is stacked on the first photodiode 240 with a N type potential well or a P type substrate of NMOS; or a PIN type photodiode of amorphous silicon (second photodiode 220) is stacked on the first photodiode 240 with a P type potential well or a N type substrate of PMOS.

Figure 6:
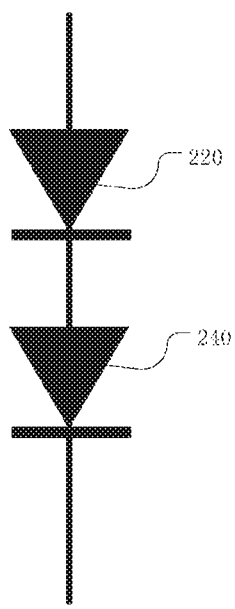
FIG. 6 to FIG. 9 are schematic views of combinations of different photodiodes according to a third embodiment of the present disclosure.
Figure 7:
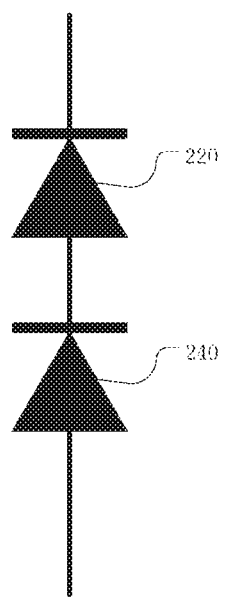

Preferably, shown in FIG. 6 and FIG. 7, the first photodiode 240 and the second photodiode 220 are connected in positive series. In FIG. 6, the first photodiode 240 is PN type, the second photodiode 220 is PIN type. One role of the arrangement is to have a smaller tray capacitance and a larger dynamic range, another role is to have characteristics of high blue response, low side wall leakage, high peripheral lag and etc. In FIG. 7, the first photodiode 240 is NP type, the second photodiode 220 is NIP type. One role of the arrangement is to have a smaller tray capacitance and a larger dynamic range, another role is to have high channel mobility.

Figure 8:
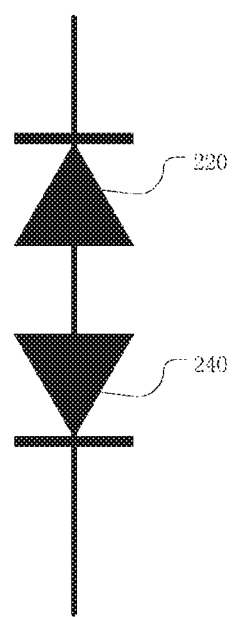
Figure 9:
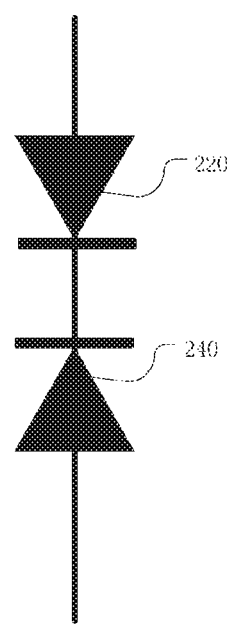

In other embodiments, shown in FIG. 8 and FIG. 9, the first photodiode 240 and the second photodiode are connected in reversed series. In FIG. 8, the first photodiode 240 is PN type, the second photodiode 220 is NIP type. By this arrangement results in less side wall leakage current of the second photodiode 220, higher blue light response, and a higher mobility of the field effect transistor, to acquire a higher current gain in the amplified pixel or active sensor pixel.

Similarly, in some other cases, the embodiment shown in FIG. 9 can also be adopted. Wherein, the first photodiode 240 is NP type, the second photodiode 220 is PIN type.

Figure 10:
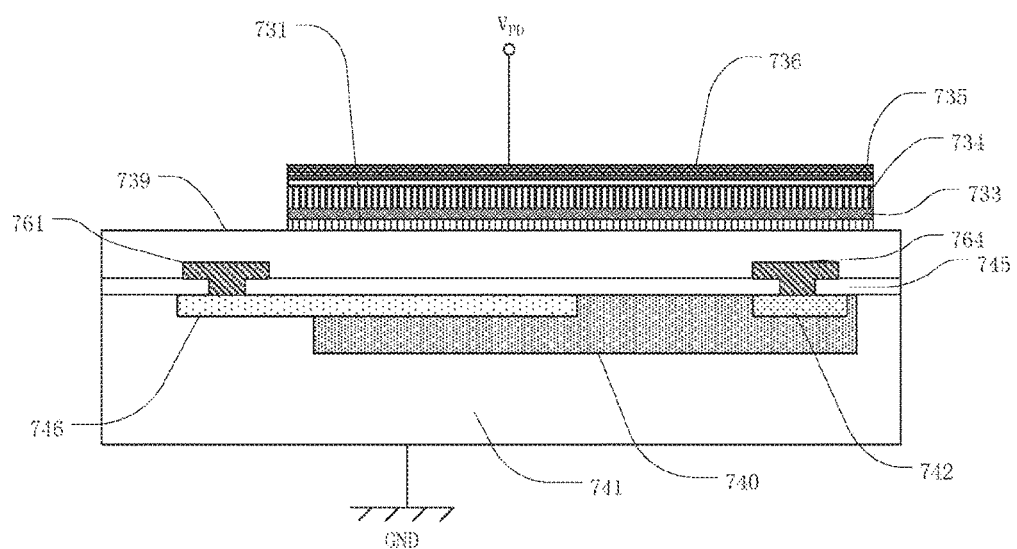
FIG. 10 is a cross-sectional view of a hybrid semiconductor device according to a fourth embodiment of the present disclosure.

FIG. 10 is a cross-sectional view of a hybrid semiconductor device according to a fourth embodiment of the present disclosure.

Shown in FIG. 10, the semiconductor device comprises a first photodiode; a second photodiode arranged on the first photodiode; and an insulating layer 745 of field oxide arranged between the first photodiode and the second photodiode. The equivalent capacitance of the insulating layer 745 can be indicated as $C_{OX}$.

The first photodiode (e.g. a crystal silicon photodiode) comprises a. P type substrate 741; a doped layer 740 of N– type formed in the substrate 741; a doped layer 742 of N+ type; a doped layer 746 of P+ type; an electrode 764 formed on the substrate and connected to the doped layer 742; and an electrode 761 connected to the doped layer 746. The electrode 761 can also function as a circuit connection component of the silicon substrate and is usually connected to ground. The equivalent capacitance of the doped layer 740 can be indicated as $C_{DEP}$. The second photodiode comprises a first transparent conductive film 731, a first doped layer 733, a un-doped a-Si layer 734, a second doped layer 735 and a second transparent conductive film 736 formed on the insulating layer 745 and an organic insulating layer 739 in a sequence. The equivalent capacitance of the second photodiode can be indicated as $C_{PD}$.

To reduce the dark charges of the first photodiode coming from the surface defect state of the insulating layer 745, a semiconductor film 746 doped of P+ type is arranged to fill in or pin up the surface defect state in advance. However, a larger stray capacitance exists between the first photodiode and the second photodiode. As the second semiconductor layer 746 is applied with a fixed voltage, $C_{DEP}$ is equivalent to infinitely large, and $C_{total}=C_{PD}+C_{OX}$. To relieve the conflict, an organic film 739 with a thickness from 1 micrometer to 5 micrometers is arranged between the insulating layer 745 and the second photodiode in this embodiment. The relative dielectric constant of the organic film 739 can be such as 2.5 to 4. The organic film 739 can be filmed by coating and baking to reduce the stray capacitance between the first photodiode and the second photodiode, and then planarize the concave and convex of the surface of the insulating layer 745.

Figure 11:
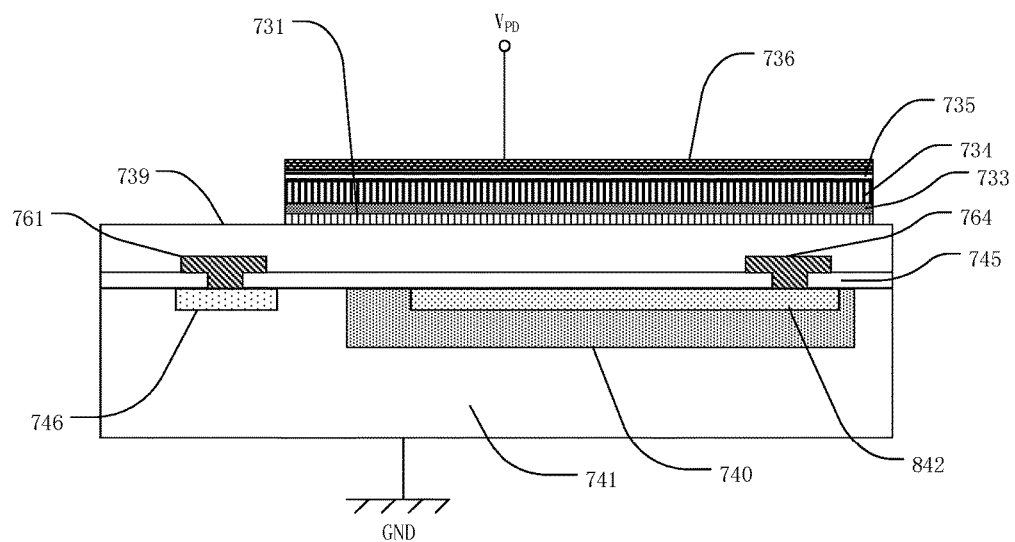
FIG. 11 is a cross-sectional view of a hybrid semiconductor device according to a fifth embodiment of the present disclosure.

FIG. 11 is a cross-sectional view of a hybrid semiconductor device according to a fifth embodiment of the present disclosure. One unique feature shown in FIG. 11 introduced in the fifth embodiment compared to the fourth embodiment is to replace the doped semiconductor film 746 of P+ type with a semiconductor layer 842 doped of N+ type replaces, which can also realize the function of pinning up the surface defect state of the insulating layer.

The doped structure of the silicon substrates shown in FIG. 10 and FIG. 11 can also be changed by exchanging the N doped type and the P doped type, to form a multispectral imaging device having a similar geometric structure and an opposite conductivity.

Shown in FIG. 10 and FIG. 11, the amorphous silicon islands of the second photodiodes completely cover the photoelectric conversion area of the first photodiode below, to prevent visible light from leaking through the intervals of the amorphous silicon islands and irradiating the infrared conversion area below.

Figure 12:
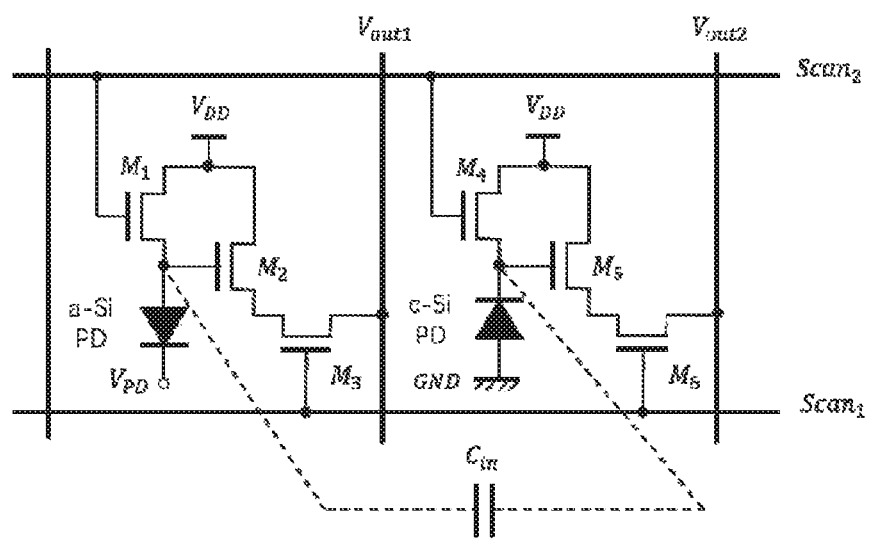
FIG. 12 is a circuit diagram of a multispectral imaging device according to a sixth embodiment of the present disclosure.

FIG. 12 is a circuit diagram of a multispectral imaging device according to a sixth embodiment of the present disclosure. The multispectral imaging device comprises a pixel array, each subpixel of the pixel array comprises three transistors and a photodiode. The photodiode can be the first photodiode or the second photodiode to convert incident light to electric signals. The three transistors can comprise an amplifier transistor to amplify the electric signal; an output transistor; and a reset transistor, to reset the potential of the photodiode. The three transistors can all be field effect transistors of crystal silicon, or at least one transistor thereof is formed by polycrystal silicon or amorphous silicon.

The left pixel comprising the second photodiode and the right pixel comprising the first photodiode in FIG. 12 are an amorphous silicon pixel and a crystal silicon pixel, respectively. Seen from a cross-sectional view of the device, the left pixel is actually stacked on the right pixel. The first photodiode 240 is NP type, and the second photodiode 220 is NIP type. Shown in FIG. 12, M1, M2, M3 are the reset transistor, the amplifier transistor and the output transistor of the second photodiode, respectively. Similarly, M4, M5, M6 are the reset transistor, the amplifier transistor, and the output transistor of the first photodiode transistor, respectively. M1 and M4 are both controlled by a scan line Scan2, M3 and M6 are both controlled by a scan line Scant adjacent to Scan2. The scan direction is from bottom to top, signal voltage is output firstly, then the pixels connected to a same line are reset. During the reset period of the pixels connected to a same line, the pixels connected to the next line are opened and output signal voltage. In the cross-sectional structural view, the second photodiode is stacked on the first photodiode, therefore, a stray capacitance $C_{in}$ in direct proportion to the covering area exists between the two photodiodes. According to the embodiment shown in FIG. 10 or FIG. 11, the stray capacitance is equal to the total capacitance of the insulating layer of field oxide and the organic insulating film connected with each other in series. When the organic insulating film is thick enough, such as larger than 2 micrometers, the influence from the stray capacitance $C_{in}$ to the working performance of the second photodiode and first photodiode can be omitted.

It should be stated that, the embodiments described previously combining FIG. 1 to FIG. 12 are representing one or several aspects in arrangements, combinations and features of the present disclosure, but not limit the scope of the present disclosure. For example, the arrangements, combinations of subpixels and the connection relationships of the subpixels, the data lines and the scan lines are not limited to this. The semiconductor devices shown in the figures include at least four technical aspects: circuits and structure; manufacture process and processing parameters; materials of semiconductors, metals and insulating films; actuating methods in actual use. The contents disclosed in the four aspects and with various combinations or varieties thereof, should all be understood to be in accordance with the basic conception of the present disclosure. Other semiconductor materials, include polycrystal silicon, microcrystal silicon, amorphous selenium, semiconductor of III-V system, semiconductor of II-IV system, metal oxide semiconductor, and etc, can be used to replace the a-SiH as the visible light conversion material. The transistors in each subpixel may also be replaced by low temperature polycrystal silicon TFT (LIPS TFT), metal oxide semiconductor such as IGZO TFT, CdTe TFT, organic semiconductor TFT, and etc.

On that account, with the multispectral imaging device of the present disclosure, the conversion area of the first photodiode is completely or partially depleted during working period, to have a smaller stray capacitance between the first photodiode and the second photodiode, to decrease cross-talk between different photodiodes, and then increase the efficiency of converting signal charges to signal voltage.

Above all, the second photodiode and the first photodiode are overlapped with each other along the light path, but realize the functions of light absorption and light conversion aiming at different wavebands, respectively. Seen from the channels for storage and transmission of signal charges, with the arrangement of the present disclosure, the influence between the two photodiodes can all be adequately prevented, no matter in a case that each pixel comprising at least one of the two photodiodes simply reads out the photo-generated charges, or in another case that each pixel has a signal amplifying or conversion from charges to voltage function, or in another case that each pixel is APS type. The present disclosure provides a technical approach and a device structure of effectively acquiring a color image of at least one color and a gray (intensity) image of at least one infrared light waveband at the same time. The level of medical imaging diagnosis and treatment can be improved significantly by acquiring multispectral images, especially infrared images information of subcutaneous tissues effectively, portably and accurately.

The basic concept and a plurality of embodiments of the present disclosure are described above. Here a statement need to be made that the present disclosure is not limited by the above specific embodiments, the person skilled in the art may make all kinds of transformations and amendments and combinations within the scope of claims, which will not influence the actual contents of the present disclosure. The present disclosure is also not limited to medical imaging application as described in the present disclosure, it may also be used in other fields such as industrial and agriculture products, environment monitoring and diagnosis, recognition of personal identity, instruments in gaming industry, virtual reality and augmented reality and etc.

What is claimed is:

1. A multispectral imaging device, comprising a hybrid semiconductor device of stacked type to separate different wavebands in a three-dimensional space, said hybrid semiconductor device comprising:
    a first photodiode, configured to convert NIR light photons to electrons, wherein a first plurality of said first photodiode forms a detecting array of infrared light image, said first photodiode comprising a substrate and a depletion layer formed in said substrate, wherein said first photodiode is made of crystal silicon material; and
    a second photodiode, arranged on said first photodiode, configured to convert visible light photons to electrons, wherein a second plurality of said second photodiode of forms a detecting array of visible light image, said second photodiode is NIP or PIN type, and said second photodiode is made of hydrogenated amorphous silicon material;
    said multispectral imaging device comprising a plurality of sub-pixels comprising a plurality of first kind of sub-pixels and a plurality of second kind of sub-pixels, wherein each of said sub-pixels comprises at least:
    a photodiode for converting light to electric signals, an amplifier transistor for amplifying said electric signal, an output transistor for outputting an amplified electric signal, and a reset transistor for resetting a potential of said photodiode; wherein said photodiode is made of said first photodiode in said first kind of sub-pixel or made of said second photodiode in the second kind of sub-pixel.

2. The multispectral imaging device according to claim 1, wherein, said depletion layer is covered completely by a vertical projection of said second photodiode on a plane of said substrate.

3. The multispectral imaging device according to claim 1, wherein,
    said second photodiode is NIP type, said first photodiode is NP type; or
    said second photodiode is PIN type, said first photodiode is PN type.

4. The multispectral imaging device according to claim 1, wherein,
    said second photodiode is PIN type, said first photodiode is NP type; or
    said second photodiode is NIP type, said first photodiode is PN type.

5. The multispectral imaging device according to claim 1, wherein, said second photodiode comprises a first transparent conductive film, an a-Si doped layer of N+ type, an a-Si un-doped layer, an a-Si doped layer of P+ type and a second transparent conductive film.

6. The multispectral imaging device according to claim 1, further comprising:
    an isolating component, arranged between a semiconductor layer and said depletion layer on a plane of said substrate.

7. The multispectral imaging device according to claim 1, further comprising:
   an organic film layer filmed by coating and an insulating layer of field oxide, arranged between said first photodiode and said second photodiode.

8. The multispectral imaging device according to claim 7, wherein a thickness of said organic film layer is in a range of 1 micrometer to 5 micrometers.

9. The multispectral imaging device according to claim 7, wherein a relative dielectric constant of said organic film is in a range of 2.5 to 4.

10. The multispectral imaging device according to claim 7, wherein said depletion layer comprises a N type potential well, and said depletion layer is formed by N– doping and activation with a method of ion implantation between the substrate of P type and said insulating layer.

11. The multispectral imaging device according to claim 7, wherein said depletion layer comprises a P type potential well, and said depletion layer is formed by P– doping and activation with a manner of ion implantation between a N type substrate and said insulating layer.

12. The multispectral imaging device according to claim 1, wherein said substrate is N type or P type, and correspondingly, said depletion layer is a hole depletion layer or an electron depletion layer.

13. The multispectral imaging device according to claim 1, wherein a thickness of said depletion layer is in a range of 2 micrometers to 100 micrometers.

14. The multispectral imaging device according to claim 1, wherein said detecting array of infrared light image comprises a first photodiode array having depletion layers with at least two kinds of thicknesses.

* * * * *